United States Patent
Guo et al.

(10) Patent No.: US 8,859,316 B2
(45) Date of Patent: Oct. 14, 2014

(54) SCHOTTKY JUNCTION SI NANOWIRE FIELD-EFFECT BIO-SENSOR/MOLECULE DETECTOR

(75) Inventors: Dechao Guo, Wappingers Falls, NY (US); Christian Lavoie, Ossining, NY (US); Christine Ouyang Qiqing, Yorktown Heights, NY (US); Yanning Sun, Scarsdale, NY (US); Zhen Zhang, Ossining, NY (US)

(73) Assignee: International Business Machines Corporation, Armonk, NY (US)

( * ) Notice: Subject to any disclaimer, the term of this patent is extended or adjusted under 35 U.S.C. 154(b) by 851 days.

(21) Appl. No.: 12/825,527

(22) Filed: Jun. 29, 2010

(65) Prior Publication Data

US 2011/0316565 A1   Dec. 29, 2011

(51) Int. Cl.
*H01L 21/00* (2006.01)
*H01L 29/06* (2006.01)
*G01N 27/414* (2006.01)

(52) U.S. Cl.
CPC ........ *G01N 27/4145* (2013.01); *H01L 29/0673* (2013.01); *G01N 27/4146* (2013.01)
USPC ............. 438/49; 257/252; 257/253; 257/414; 257/9; 257/27; 257/E51.04

(58) Field of Classification Search
None
See application file for complete search history.

(56) References Cited

U.S. PATENT DOCUMENTS

| 6,893,930 B1 * | 5/2005 | Yu et al. ................ 438/305 |
| 7,394,118 B2 * | 7/2008 | Zhou .......................... 257/253 |
| 7,582,500 B2 * | 9/2009 | Chou et al. .................. 438/49 |
| 2007/0132043 A1 * | 6/2007 | Bradley et al. ................ 257/414 |
| 2007/0155037 A1 * | 7/2007 | Chou et al. .................. 438/49 |
| 2008/0012067 A1 * | 1/2008 | Wu ............................ 257/330 |
| 2009/0152527 A1 * | 6/2009 | Lee et al. ....................... 257/9 |
| 2010/0198521 A1 * | 8/2010 | Haick .......................... 702/19 |
| 2012/0153359 A1 * | 6/2012 | Frye et al. .................... 257/213 |

OTHER PUBLICATIONS

Michael Quirk and Julian Serda; Semiconductor Manufacturing Technology; 2001; Pearson Education International; p. 465.*
Michael Quirk and Julian Serda; Semiconductor Manufacturing Technology; 2001; Pearson Education International; pp. 278, 279 and 465.*

* cited by examiner

*Primary Examiner* — Matthew W Such
*Assistant Examiner* — Samuel Lair
(74) *Attorney, Agent, or Firm* — Novak Druce Connolly Bove + Quigg LLP; Louis J. Percello, Esq.

(57) ABSTRACT

A Schottky junction silicon nanowire field-effect biosensor/molecule detector with a nanowire thickness of 10 nanometer or less and an aligned source/drain workfunction for increased sensitivity. The nanowire channel is coated with a surface treatment to which a molecule of interest absorbs, which modulates the conductivity of the channel between the Schottky junctions sufficiently to qualitatively and quantitatively measure the presence and amount of the molecule.

15 Claims, 6 Drawing Sheets

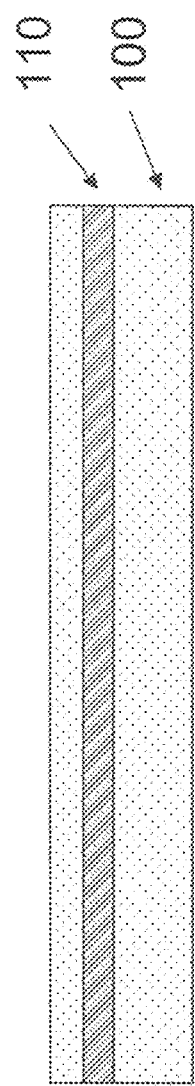
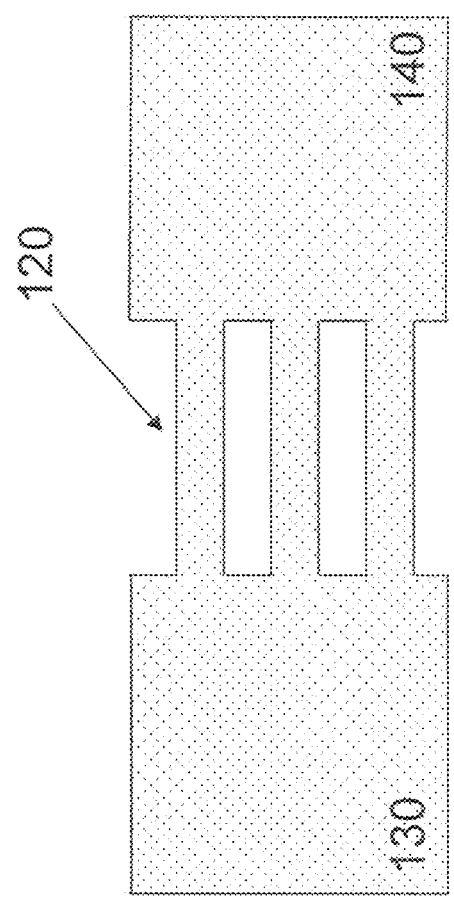

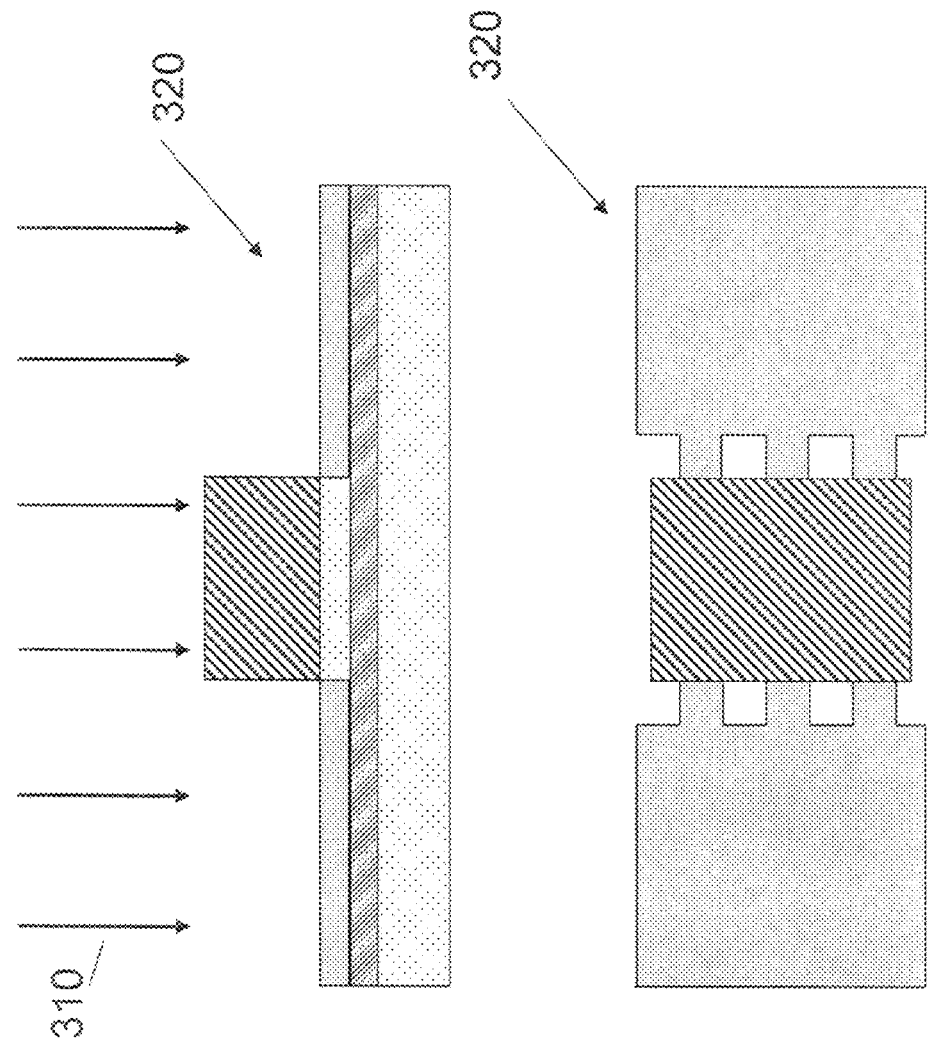

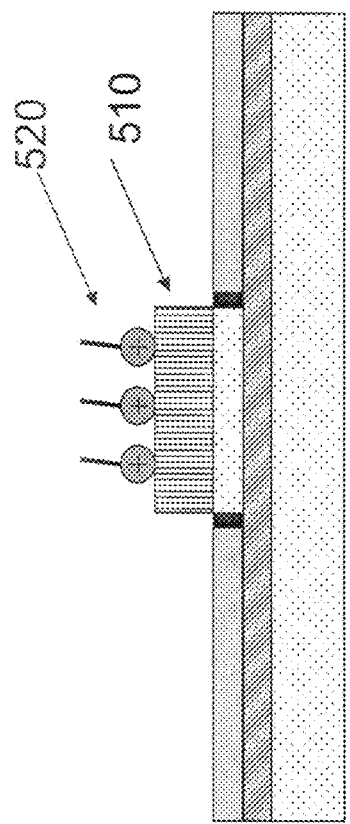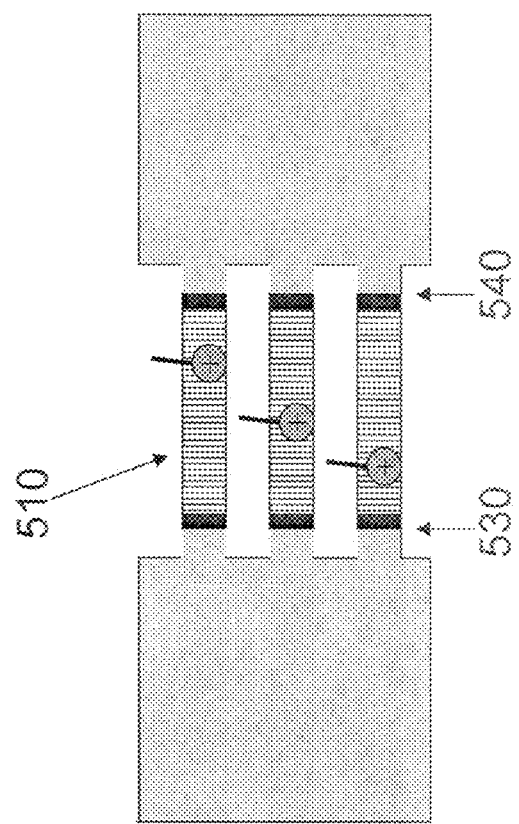

SCHOTTKY JUNCTION SI NANOWIRE FIELD-EFFECT BIO-SENSOR/MOLECULE DETECTOR

FIELD OF THE DISCLOSURE

The present disclosure relates to a Schottky junction and a method of fabricating the same. More particularly, the present disclosure relates to a nanowire field-effect biosensor/molecule detector having an increased sensitivity.

BACKGROUND

Nanoscalar electronic components, such as nanowires, have tremendous potential to accurately measure the presence and amount of molecules in solution. In particular, devices utilizing such nanoscalar components are useful to detect very low concentrations and require only small volumes in the order of a few picoliter.

The basic measurement principle is to apply a surface treatment to the nanoscalar component to which the molecule of interest can be adsorbed, based on a chemical binding preference of the molecule to the surface treatment. Upon binding of the molecule to the surface treatment, an electrical property of the nanoscalar component changes as a result of the binding. The binding preference can be the electrostatic attraction of oppositely charged ions, hydrogen bonds formed between complementary strands of DNA, or an antibody binding to an antigen. For example, the conductance of the nanoscalar channel of a field effect sensor can be modified significantly, when biased under subthreshold conditions, upon the binding of the molecule to the surface treatment and a measurement of the change in conductance allows detecting the presence of the molecule. Upon calibration with solutions containing the molecule at a known concentration, an unknown concentration can be determined from the calibration data.

Biosensors having nanoscalar components on which a surface treatment is applied are known. The sensitivity of the nanoscalar components increases with decreasing thickness of the components. Further, a decreased thickness allows the incorporation into devices for small sample volumes. However, it has been found that the thickness of the nanoscalar component may not be decreased beyond a certain point because processing conditions, such as the implantation of impurities can cause decrystallization of the semiconductor material of the nanoscalar component resulting in amorphous regions. Such amorphous material is no longer suitable for the intended measurement because the resistivity increases significantly. For nanoscalar components with a thickness of several tenths of a nanometer, recrystallization with accompanying decrease in resistivity can be satisfactorily obtained by an annealing step. However, for ultra-thin nanoscalar components, i.e. for thicknesses below 10 nanometer, recrystallization cannot be achieved satisfactorily. Thus, low resistance channels cannot be formed.

Schottky source/drain (S/D) structures are an alternative because decrystallized silicon can be replaced by much more conductive metal silicides. However, ordinarily Schottky S/D structures on the above-described thicknesses of 10 nanometer or less suffer from misaligned workfunctions resulting in degraded subthreshold slope, which determines the device sensitivity. The sensitivities of devices with a degrades subthreshold slope are insufficient for the low detection levels envisioned herein.

SUMMARY OF THE DISCLOSURE

Described herein is a Schottky junction field-effect sensor with a nanoscalar component having a thickness in the order of about 10 nanometer and less and a method of manufacturing the same. In a typical embodiment, the Schottky junction field-effect sensor comprises an insulator layer on a semiconductor substrate, a channel region between a first electrode and a second electrode, wherein the channel region, the first electrode, and the second electrode are provided on the insulator layer, a surface coating on the channel region, and a first interfacial layer between the first electrode and the channel region and a second interfacial layer between the second electrode and the channel region, wherein the first interfacial layer modifies the Schottky barrier height between the first electrode and the channel region and the second interfacial layer modifies the Schottky barrier height between the second electrode and the channel region.

Additionally, a method of measuring a concentration of a molecule is described, which comprises immersing a Schottky field-effect sensor in a solution of the molecule, adsorbing the molecule to the surface coating, and measuring a change of a conductance of the channel region at subthreshold back gate bias.

Further described is a method of manufacturing a Schottky junction field-effect sensor, that comprises thinning a semiconductor layer of a semiconductor substrate with an embedded insulator, forming a channel region, a first electrode region, and a second electrode region within the semiconductor layer and abutting the embedded insulator, depositing a silicon nitride layer on the channel region, patterning the silicon nitride layer, converting the first electrode region and the second electrode region into a metal silicide, thereby forming a first electrode and a second electrode, implanting an impurity by blanket implantation, diffusing the impurity to an interface between the channel region and the metal silicide by annealing, removing the silicon nitride layer; and providing a surface treatment of the channel region.

The Schottky junction determines the sensitivity of the field effect sensor. Described in this disclosure are Schottky junction field effect sensors with aligned source/drain workfunctions, wherein workfunction alignment is achieved by implantation of impurities and subsequent segregation towards the silicide/silicon channel interfaces.

BRIEF DESCRIPTION OF THE DRAWINGS

The foregoing and other objects, aspects and advantages will be better understood from the following detailed description of the best and various embodiments with reference to the drawings, in which:

FIG. 1a shows a first view of a patterned semiconductor substrate 100 with an imbedded dielectric layer 110.

FIG. 1b shows a view perpendicular to the direction of the first view in FIG. 1a. In particular, shown are three channel regions 120, which are located between first electrode 130 and second electrode 140.

FIG. 3a and FIG. 3b show the silicide formation for converting the region of the patterned semiconductor structure abutting the silicon nitride layer into a metal silicide, followed by a blanket implantation process (310) for implanting an impurity into the metal silicide.

FIGS. 5a and 5b show a surface treatment 510 applied to the channel region after the removal of the silicon nitride layer 210. Molecules 520 contained in solution absorb to the surface treatment 510.

DESCRIPTION OF THE BEST AND VARIOUS EMBODIMENTS

Turning to the drawings, FIGS. 1a and 1b show an early processing step in the formation of Schottky junction field-effect sensor with a nanowire 120 being formed between two electrodes 130 and 140. As described in detail below, the nanowire 120 will form the channel region of the Schottky junction field-effect sensor. In this particular embodiment, three nanowires are formed between the electrodes, but the number of nanowires is not particularly limited as structures including one, two or more than three nanowires are also within the scope of this disclosure. The structure of a nanowire and two electrodes is typically formed by a lithographic process. Also typically, substrate 100 in FIG. 1a is silicon.

With particularity, the imbedded dielectric layer 110 shown in FIG. 1a is silicon dioxide, but other dielectric materials may also be used.

Typically, the channel region of the Schottky junction field-effect sensor has a thickness of 10 nanometers or less. With particularity, the channel region is a nanowire, which, further, may be a single-crystalline material, such as single-crystalline silicone. However, the channel region can also be another semiconductor material known to the skilled artisan, such as germanium or gallium-arsenide. The length of the channel region is typically of from about 10 nanometer to about 100 micrometer.

Figure 2A:
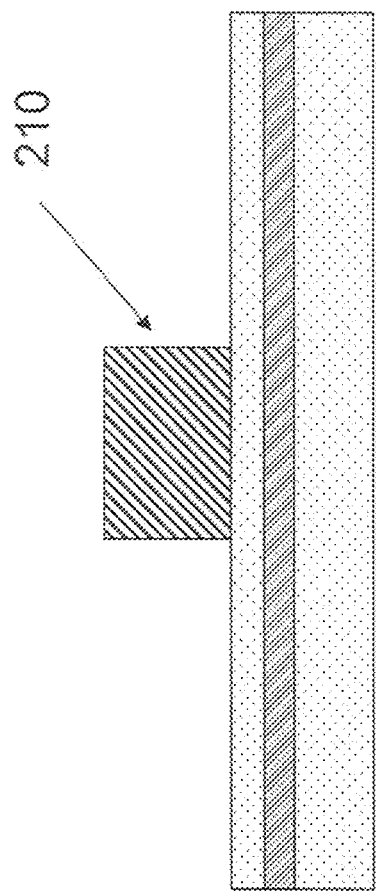
FIG. 2a shows a silicon nitride layer 210 formed over channel region 120.

As shown in FIG. 2a a silicon nitride layer 210 is formed over channel region 120. For example, the silicon nitride layer may be formed using chemical vapor deposition (CVD), or with particularity, plasma-enhanced chemical vapor deposition (PECVD). However, other methods of forming a silicon nitride layer, such as the diimine synthesis or carbothermal reduction may also be used. The silicon nitride layer defines the area that is not converted into a metal silicide in the subsequent processing step. Moreover, the silicon nitride layer prevents diffusion into the semiconductor material of channel region 120.

Figure 2B:
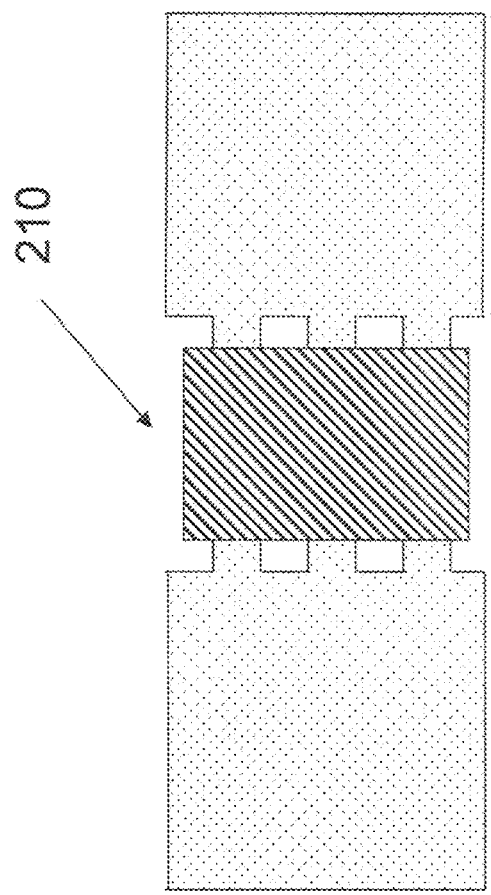
FIG. 2b shows the structure of FIG. 2a from the same viewing direction as FIG. 1b.

FIG. 2b shows the structure of FIG. 2a from the same view as FIG. 1b. As used herein, FIGS. 1a, 2a, 3a, 4a, and 5a are shown from the same point of view and FIGS. 1b, 2b, 3b, 4b, and 5b are shown from the same point of view, the viewing axes between the two groups of figures being perpendicular to each other.

As seen at FIGS. 3a and 3b show the substrate after a patterning step has been performed to partially removing the silicon nitride layer over the regions forming the electrodes 130 and 140. The regions of the semiconductor substrate, which are not covered by silicon nitride layer 210, are converted into a metal silicide layer 310. Typically, metal silicide layer 310 is formed by depositing a layer of metal, such as nickel, over the substrate and annealing the device, typically in a two-step process. During the annealing process, the deposited metal reacts with underlying silicon and forms the metal silicide layer. The method is not limited to nickel, but may also employ platinum, nickel platinum, cobalt, titanium, and tungsten as metals to be deposited. Subsequently, an implantation step is performed in which an impurity is implemented by blanket implantation 310 into the silicide layer.

Typical impurities are boron, arsenic, phosphorous, indium, and aluminum, in particular boron and arsenic.

The impurities diffuse to the silicide/silicon interface during a low temperature Rapid Thermal Anneal (RTA) process. The annealing treatment is typically performed at a temperature of from about 400° C. to about 650° C. The duration of the RTA process is typically of from about 5 second to about 5 minutes. More typically, the duration of the RTA process is about 30 seconds.

Accordingly, the first electrode 130 and the second electrode 140 are obtained from silicon in the form of the same metal silicide, which, with particularity, is nickel silicide.

Figure 4A:
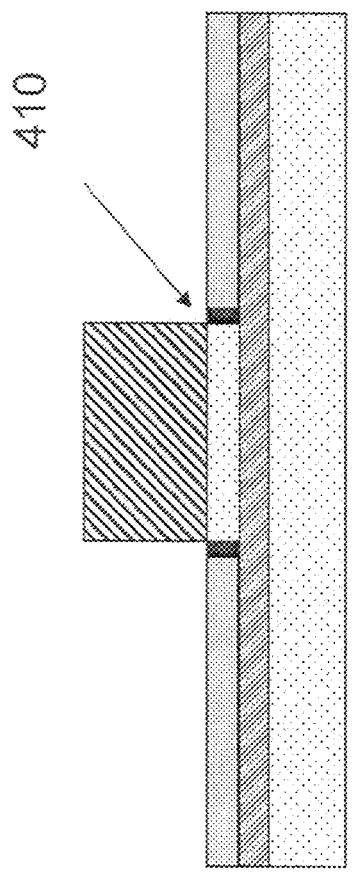
FIGS. 4a and 4b show an interface layer 410 being formed within the channel region between the metal silicide and the channel region covered by the silicon nitride after a low temperature Rapid Thermal Annealing (RTA) step to diffuse the implanted impurity into the metal silicide/channel region interface.
Figure 4B:
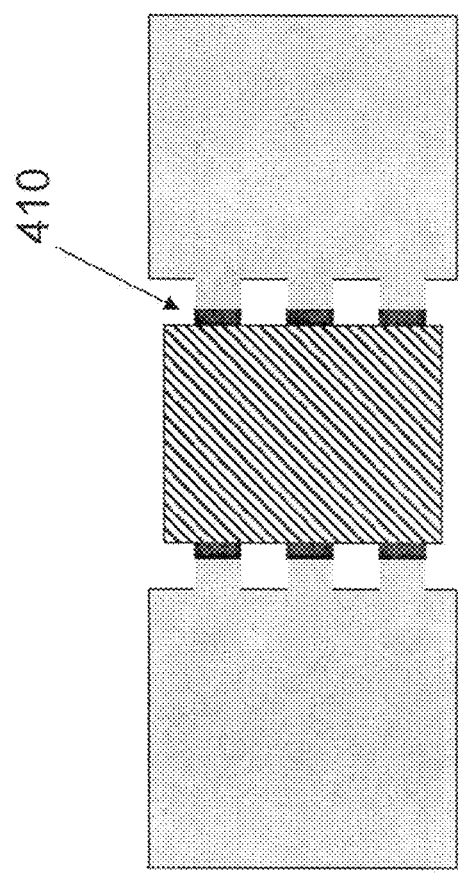

FIGS. 4a and 4b show the interface layer 410 which has been formed within the channel region between the metal silicide and the channel region covered by the silicon nitride. The impurities diffuse towards the interface layer 410 upon a further annealing step to tune the subthreshold slope of interface 410 to the desired sensitivity. The amount of the impurity at the interface, after the annealing step, is of from about $1 \cdot 10^{18}$ atoms cm$^{-3}$ to about $1 \cdot 10^{23}$ atoms cm$^{-3}$.

Thereafter, the silicon nitride layer is removed, for example with hot phosphoric acid. Specifically, the silicon nitride layer is removed by exposure to a phosphoric acid solution which, with particularity, is at a temperature of about at least 150° C.

FIGS. 5a and 5b show a surface treatment 510 applied to the channel region after the removal of the silicon nitride layer 210 and the formation of interface layer 410. Molecules 520 contained in solution absorb to the surface treatment 510 in a specific binding process. For example, surface treatment 510 may comprise a carboxylate group, a single-stranded DNA sequence or an antigen. A proton binding to a carboxylate group COO$^-$, an antibody binding to the antigen, or a DNA sequence binding to a complementary DNA sequence constitute specific adsorptions to surface treatment 510, which are detectable and quantifiably with the Schottky junction disclosed herein.

Figure 6:
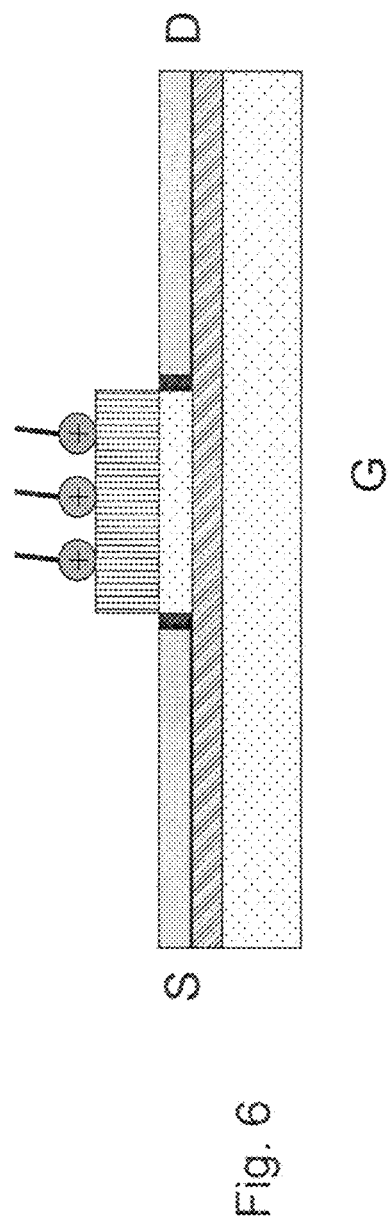
FIG. 6 shows the biasing schematic during measurements with the channel being biased to the subthreshold condition.

FIG. 6 shows the biasing condition when a measurement takes place. One electrode adjacent to channel region 120 is held as source (S) and the other electrode is held as drain (D). The channel is turned on when the substrate back below the insulator in the semiconductor on insulator SOI substrate functions as gate (G). Under these biasing conditions, the subthreshold region, with back gate bias from the substrate electrodes (G), has a conductance of the channel that is most sensitive to the potential change of the channel induced by the attached molecules. By contrast, when the substrate electrode (G) is unbiased, the conductance of the channel decreases and the channel is turned off.

In a typical measurement to determine the concentration of molecule 520 in solution, the conductance of channel region 120 is measured in a solvent to take a blank measurement. Specifically, the Schottky junction field effect sensor is immersed in a solvent and the substrate electrode (G) is biased to turn the channel on. The solvent is subsequently replaced by a solution containing molecule 520, which is the molecule of interest, in the same solvent as the blank measurement and the conductance is measured again. By measuring the conductance with known concentrations of molecule 520 a calibration curve is obtained from which the concentration of an unknown can be determined through conductance measurement. Thus, the measurement can be performed quantitatively to identify the concentration of molecule 520 in solution.

Typically, the solvent is water. However, aliphatic alcohols, such as methanol or ethanol, acetonitrile and dimethylsulfoxide (DMSO) may also be used as solvents.

The embodiments described hereinabove are further intended to explain best modes known of practicing it and to enable others skilled in the art to utilize the disclosure in such, or other, embodiments and with the various modifications required by the particular applications or uses. Accordingly, the description is not intended to limit it to the form disclosed herein. Also, it is intended that the appended claims be construed to include alternative embodiments.

The foregoing description of the disclosure illustrates and describes the present disclosure. Additionally, the disclosure shows and describes only the preferred embodiments hut, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All publications, patents and patent applications cited in this specification are herein incorporated by reference, and for any and all purpose, as if each individual publication, patent or patent application were specifically and individually indicated to be incorporated by reference. In the case of inconsistencies, the present disclosure will prevail.

What is claimed is:

1. A method of manufacturing a Schottky junction field-effect sensor, comprising:
    thinning a semiconductor layer of a semiconductor substrate with an embedded dielectric layer;
    forming a channel region, a first electrode region, and a second electrode region within the semiconductor layer and abutting the embedded dielectric layer;
    depositing a silicon nitride layer on the entire width of the channel region;
    patterning the silicon nitride layer;
    converting the first electrode region and the second electrode region into a metal silicide, thereby forming a first electrode and a second electrode;
    implanting an impurity by blanket implantation, wherein the impurity is selected from the group consisting of boron, arsenic, indium, phosphorous, and aluminum;
    diffusing the impurity to an interface between the channel region and the metal silicide by Thermal Rapid Annealing to form an interface layer comprising the impurity in an amount of about $1 \cdot 10^{18}$ atoms cm$^{-3}$ to about $1 \cdot 10^{23}$ atoms cm$^{-3}$ within the channel region between the metal silicide and the channel region covered by the silicon nitride;
    removing the silicon nitride layer; and
    providing a surface treatment of the channel region.

2. The method according to claim 1, wherein the metal of the metal silicide is selected from the group consisting of nickel, platinum, nickel platinum, cobalt, titanium, and tungsten.

3. The method according to claim 2, wherein the metal is nickel.

4. The method of claim 1, wherein the annealing is performed at a temperature of from about 400° C. to about 650° C.

5. The method of claim 1, wherein the embedded dielectric layer is silicon dioxide.

6. The method of claim 1, wherein the removing the silicon nitride layer comprises exposing the silicon nitride layer to a phosphoric acid solution.

7. The method according to claim 6, wherein the phosphoric acid solution is at a temperature of about at least 150° C.

8. The method according to claim 4, wherein the annealing is a performed for about 5 seconds to about 5 minutes.

9. The method according to claim 2, wherein the metal of the metal silicide is nickel.

10. The method according to claim 1, wherein the silicon nitride layer is formed using chemical vapor deposition.

11. The method according to claim 10, wherein the chemical vapor deposition is plasma-enhanced chemical vapor deposition.

12. The method according to claim 1, wherein the channel region is a nanowire with a thickness of 10 nanometers or less.

13. The method according to claim 1, wherein the channel region is a single crystalline material.

14. The method according to claim 13, wherein the single crystalline material is single crystalline silicone.

15. The method according to claim 1, wherein the channel region is germanium or gallium-arsenide.

* * * * *